US010951715B2

(12) United States Patent
Hart et al.

(10) Patent No.: US 10,951,715 B2
(45) Date of Patent: Mar. 16, 2021

(54) SYSTEMS AND METHODS FOR GENERATING AN ANONYMOUS INTERACTIVE DISPLAY IN AN EXTENDED TIMEOUT PERIOD

(71) Applicant: HeartFlow, Inc., Redwood City, CA (US)

(72) Inventors: Gregory R. Hart, Hayden Lake, ID (US); Gregory Paik, San Francisco, CA (US); Jeffrey Golda, Menlo Park, CA (US); Amal Khandelwal, Redwood City, CA (US); Razik Yousfi, Burlingame, CA (US)

(73) Assignee: HeartFlow, Inc., Redwood City, CA (US)

( * ) Notice: Subject to any disclaimer, the term of this patent is extended or adjusted under 35 U.S.C. 154(b) by 126 days.

(21) Appl. No.: 16/115,056

(22) Filed: Aug. 28, 2018

(65) Prior Publication Data
US 2019/0068722 A1 Feb. 28, 2019

Related U.S. Application Data

(60) Provisional application No. 62/551,672, filed on Aug. 29, 2017.

(51) Int. Cl.
*H04L 29/08* (2006.01)
*H04L 29/06* (2006.01)
*G16H 40/60* (2018.01)
*G16H 10/60* (2018.01)
*G06F 21/62* (2013.01)
*H04N 1/00* (2006.01)
*G06F 3/0481* (2013.01)

(52) U.S. Cl.
CPC ........ *H04L 67/145* (2013.01); *G06F 21/6245* (2013.01); *G16H 10/60* (2018.01); *G16H 40/60* (2018.01); *H04L 67/22* (2013.01); *H04L 69/28* (2013.01); *H04N 1/00506* (2013.01); *G06F 3/04815* (2013.01); *G06F 21/6218* (2013.01)

(58) Field of Classification Search
CPC ...... H04L 67/145; G16H 10/60; G16H 40/60; G16H 50/20; G06F 19/30; G06F 3/0481; G06F 21/62; G06F 21/6245; G06F 21/6263; H04N 1/00501; H04N 1/00506
See application file for complete search history.

(56) References Cited

U.S. PATENT DOCUMENTS 7,650,641 B2 * 1/2010 Veselova ............. G06F 21/6245
705/50
8,315,812 B2 11/2012 Taylor
8,548,778 B1 10/2013 Hart et al.
(Continued)

OTHER PUBLICATIONS

Anonymous: "HIPAA Security Series—4 Security Standards: Technical Safeguards", Mar. 31, 2007, pp. 1-17.

*Primary Examiner* — Aaron N Strange
(74) *Attorney, Agent, or Firm* — Bookoff McAndrews, PLLC

(57) ABSTRACT

Systems and methods are disclosed for displaying health data during a security timeout. One method includes: displaying an interactive interface; receiving a data type included in the display; detecting a timeout of the interactive interface; hiding or removing the data type from the display in response to the timeout; and initiating an extended timeout including the display with the data type removed.

18 Claims, 12 Drawing Sheets

(56) References Cited

U.S. PATENT DOCUMENTS

| | | | |
|---|---|---|---|
| 8,555,336 B1* | 10/2013 | Dhesi | H04L 63/08 |
| | | | 455/26.1 |
| 9,003,551 B2* | 4/2015 | Hoyer | G06F 21/6245 |
| | | | 726/19 |
| 9,898,610 B1* | 2/2018 | Hadsall | G06K 9/20 |
| 9,977,909 B1* | 5/2018 | Austin | G06F 3/04883 |
| 10,311,249 B2* | 6/2019 | Sharifi | G06F 21/6254 |
| 2005/0078082 A1* | 4/2005 | Muralidharan | G16H 40/63 |
| | | | 345/156 |
| 2007/0006316 A1 | 1/2007 | Veselova et al. | |
| 2007/0234219 A1* | 10/2007 | Bhattaru | G16H 10/60 |
| | | | 715/744 |
| 2008/0177569 A1* | 7/2008 | Chen | G06F 21/32 |
| | | | 705/2 |
| 2012/0233671 A1 | 9/2012 | Beder et al. | |
| 2014/0047523 A1* | 2/2014 | Swerdlow | G06F 21/62 |
| | | | 726/7 |
| 2014/0208418 A1 | 7/2014 | Libin | |
| 2014/0259184 A1 | 9/2014 | Hoyer | |
| 2014/0283142 A1* | 9/2014 | Shepherd | G06F 3/0482 |
| | | | 726/30 |
| 2014/0366158 A1* | 12/2014 | Han | G06F 21/32 |
| | | | 726/28 |
| 2016/0224780 A1* | 8/2016 | Kukreja | G06F 21/44 |
| 2016/0371505 A1* | 12/2016 | Blanchard | G06F 21/6245 |
| 2018/0137938 A1* | 5/2018 | Vaddiraju | A61B 5/0004 |
| 2018/0285592 A1* | 10/2018 | Sharifi | G06F 21/6245 |
| 2019/0080112 A1* | 3/2019 | Adams | G06F 3/0481 |

* cited by examiner

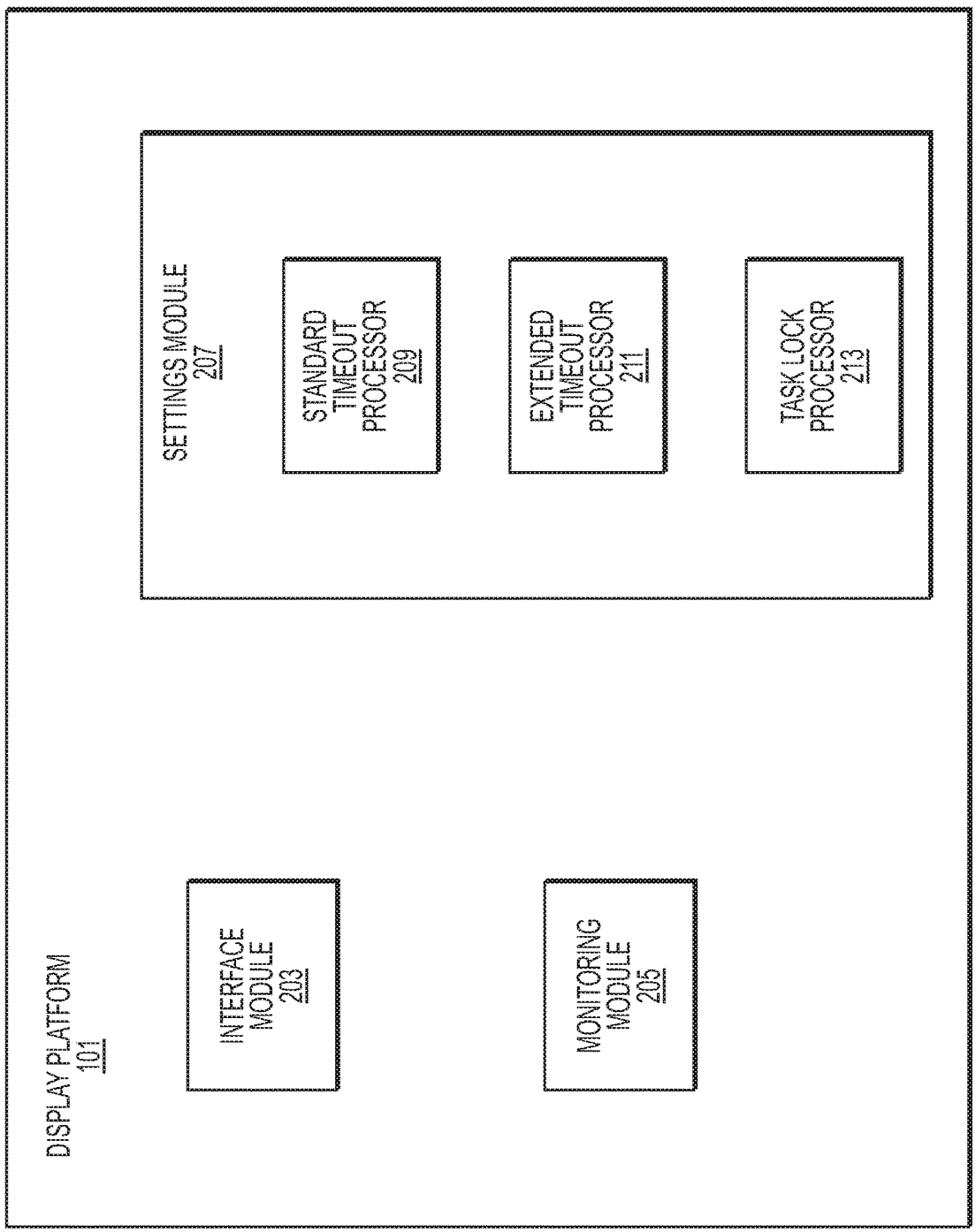

SYSTEMS AND METHODS FOR GENERATING AN ANONYMOUS INTERACTIVE DISPLAY IN AN EXTENDED TIMEOUT PERIOD

RELATED APPLICATION

This application claims priority to U.S. Provisional Application No. 62/551,672, filed on Aug. 29, 2017, the entire disclosure of which is hereby incorporated by reference in its entirety.

TECHNICAL FIELD

Various embodiments of the present disclosure relate generally to interactive displays containing patient privacy information, e.g., in a medical or healthcare setting. Specifically, particular embodiments of the present disclosure relate to systems and methods for providing an extended timeout period after a security timeout, where the extended timeout may provide an interactive interface for a medical professional while securing patient privacy information.

INTRODUCTION

In facilities within hospitals, clinics, and medical research centers, physicians, medical personnel, and researchers are often called to perform research, or diagnostic/therapeutic procedures based on patient-specific data. For example, in a catheterization lab (cath lab), a user may have to perform analysis on patient-specific models or data, which may result in inputting specific parameters or changes, or viewing or manipulating simulations of the model. In order to safeguard private patient information (e.g., as a part of security certification), current systems providing tools (e.g., interactive diagnostic services) for such analyses may "time out" after a period of inactivity, and the work that a user's work may be lost. Such systems may time out from a perceived inactivity. Meanwhile, the "perceived inactivity" may in fact be while a user is actively using or referencing the tool. For example, a user may be using the tool as a reference for an ongoing procedure being performed on a patient. Accordingly, such tools/apps may be frustrating to use, frequently timing out mid-procedure, and sometimes causing the user's work to be lost or forcing a user's work to be interrupted. Since the timeout feature may not be eliminated from most tools or apps as a result of security certifications and privacy standards, current apps or tools for patient-specific analyses impair or discourage a user's ability to use such tools or apps for analysis and hinder patient care.

Therefore, there is a need for a system and method for providing the health care professional with a positive user experience, for example, in the cath lab, while ensuring that security controls are in place to protect patient privacy information, so that more patients may be treated. The present disclosure is directed to overcoming one or more of the above-mentioned problems or interests.

SUMMARY

According to certain aspects of the present disclosure, systems and methods are disclosed for provide an interactive interface for a medical professional while securing patient privacy information. One method of displaying health data during a security timeout includes: displaying an interactive interface; receiving a data type included in the display; detecting a timeout of the interactive interface; hiding or removing the data type from the display in response to the timeout; and initiating an extended timeout including the display with the data type removed.

According to another embodiment, a system is disclosed for displaying health data during a security timeout. The system includes a data storage device storing instructions for displaying health data during a security timeout; and a processor configured to execute the instructions to perform a method including the steps of: displaying an interactive interface; receiving a data type included in the display; detecting a timeout of the interactive interface; hiding or removing the data type from the display in response to the timeout; and initiating an extended timeout including the display with the data type removed.

In accordance with yet another embodiment, a non-transitory computer readable medium for use on a computer system containing computer-executable programming instructions for performing a method of displaying health data during a security timeout. The method includes: displaying an interactive interface; receiving a data type included in the display; detecting a timeout of the interactive interface; hiding or removing the data type from the display in response to the timeout; and initiating an extended timeout including the display with the data type removed.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIG. 2 block diagram of a display platform for preparing interactive displays for medical diagnostics, according to an exemplary embodiment of the present disclosure.

Figure 1A:
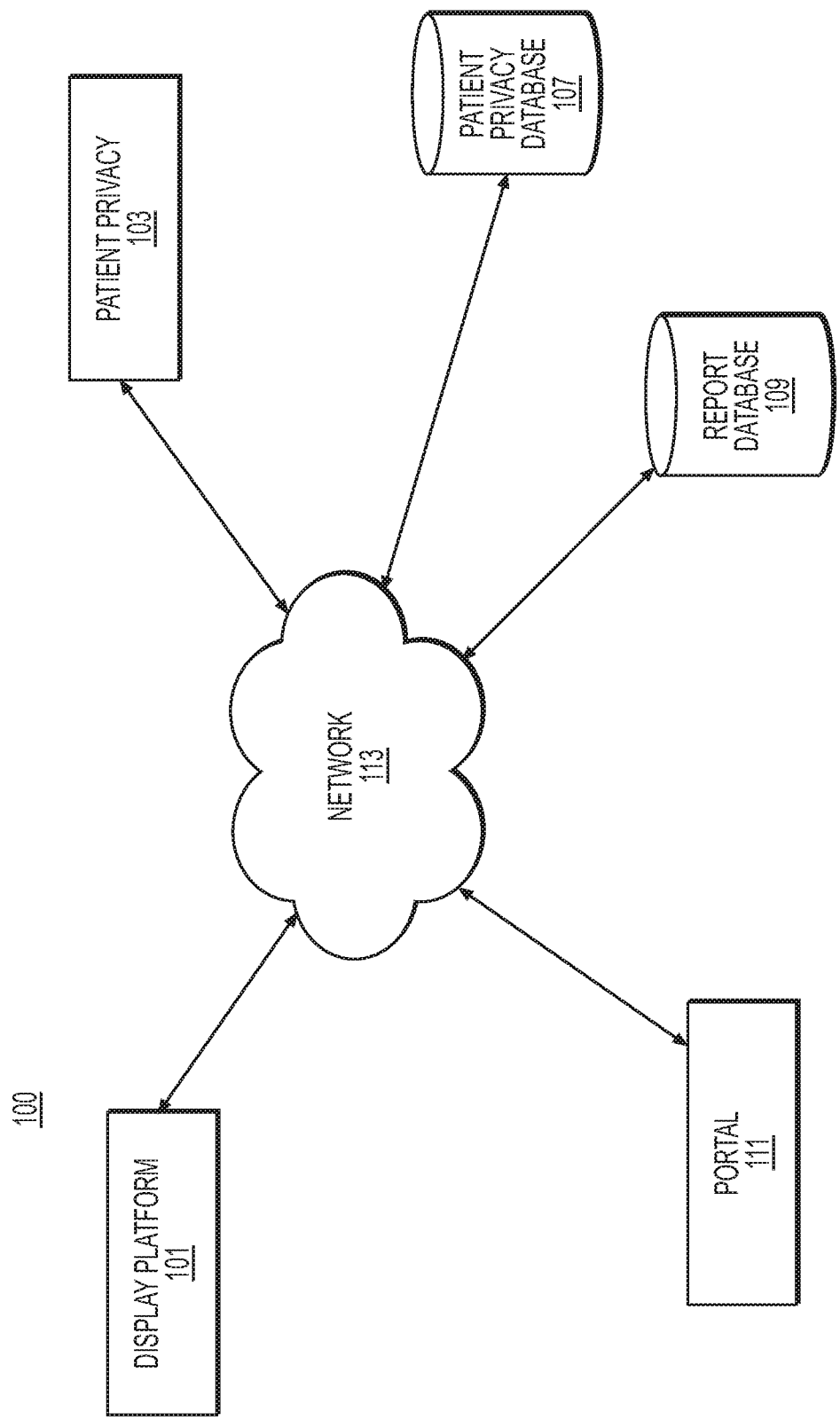
FIG. 1A depicts an exemplary interactive diagnostic system 100 offering a display, according to an exemplary embodiment of the present disclosure.

As used herein, the term "exemplary" is used in the sense of "example," rather than "ideal." In addition, the terms "first," "second," and the like, herein do not denote any order, quantity, or importance, but rather are used to distinguish one concept or structure from another. Moreover, the terms "a" and "an" herein do not denote a limitation of quantity, but rather denote the presence of one or more of the referenced items. For the purposes of the disclosure, "patient" may refer to any individual or person for whom diagnosis or treatment analysis (e.g., data analysis) is being performed, or any individual or person associated with the diagnosis or treatment analysis of one or more individuals.

DESCRIPTION OF THE EMBODIMENTS

Reference will now be made in detail to the exemplary embodiments of the present disclosure, examples of which are illustrated in the accompanying drawings. Wherever possible, the same reference numbers will be used throughout the drawings to refer to the same or like parts.

As described above, current patient privacy protection measures in the form of security timeouts may hinder patient care and frustrate users. Due to prevalent standards for fostering the security and privacy of private personal health information (PHI), it is infeasible to remove the timeout feature in existing systems for patient-specific analysis. The present disclosure is directed to providing an extended viewing time for the model interactive analysis, while still preserving patient privacy. In particular, the present disclosure provides an extended timeout function that may be triggered after a standard (security) timeout. During the extended timeout, a user may still have access to an interactive display or various capabilities/functions of the display, but the patient privacy information of the display may be removed or masked. For example, extended timeout may provide an interface where confidential or private personal health information of a patient may be blacked out or rendered inaccessible, while patient-specific analysis data may still be available in an interactive display for a user to view, manipulate, or modify. In other words, interactive displays during the extended timeout period may be devoid of patient privacy information.

For example, a user may be able to access and continue ongoing work related to patient-specific data (e.g., after a timeout), meaning a user may maintain access to models or test results for a patient, manipulate the models or test results, prompt re-computation or modifications to the models/test results, etc. At the same time, patient confidential and/or private information (or any information that could link the patient-specific analysis data to the identity of the patient) may be absent from the user interface. As a result, a user may preserve his or her access to the data and/or stored settings of an ongoing analysis without identifying biographical or other confidential and/or private information of the patient. The extended timeout feature may be useful during a procedure or treatment of a patient, where a user (e.g., a physician) may need to periodically access an app or tool, but cannot or does not do so at a level of frequency that prevents the app or tool from entering a mandatory or standard timeout.

In some embodiments, a user may be prompted to submit login credentials or end the extended timeout session if they attempt to access data for any other patient. In other words, to ensure Health Information Trust Alliance (HITRUST) compliance, some embodiments of the present disclosure may prevent unmonitored access to unrelated patient records. For example, various features may restrict access to system, physically, and logically. Users of the system may be informed that privacy risks may exist if there is unmonitored access to patient records. The system may also provide the user with a privacy risk warning for a timeout extension. Furthermore, the system may prompt the user for an acknowledgement and assumption of privacy risk by the user. In some embodiments, the assumption of privacy risk may extend to, or be replaced by a covered entity (e.g., insurance).

In some embodiments, the implementation of the system may include features for mitigating the control and/or access of the system. These features may include an extension of the regular timeout period for a single session. For example, the period may be extended to fifteen minutes after a user views a legal disclaimer. In other words, if the system is set to prompt a standard security timeout after five minutes of inactivity, such an embodiment may provide a fifteen minute extension such that the standard timeout is not initiated until 20 minutes of inactivity if the user is detected as having read and confirmed agreement to a legal disclaimer. Such extensions may be offered once for each session and each user, such that a user will receive an extension on the timeout only if he/she signed or verified agreement to the legal disclaimer for that particular session.

The features may further include a second login confirmation, which may require the user to have elevated system rights (e.g., after logging in). Other features, may include, but are not limited to, viewing (or enabling the viewing of) an account lock to a single patient record, and blacking out the view of some or all patient-specific information without the account lock. A user may also be prompted to "sign in to save changes," e.g., prior to a timeout. Thus, various risk mitigation features may prevent unmonitored access to unrelated patient records, inform users with appropriate rights about risk, and allow exceptions on a user-by-user basis in the form of elevated system rights.

In summary, the present disclosure describes systems and methods of presenting access to non-confidential and/or non-private information (and the ability to manipulate that information, in some cases), while complying with security protocols that require a "timeout" to protect confidential and/or private information. In this way, physicians and clinicians may continue to use a tool without exposing patient identifying information or being asked repeatedly to sign in. At the same time, cybersecurity officers of healthcare providers may be assured that patient health information is protected by timeout functions, and diagnostic service providers (e.g., tool/app providers) may provide a positive user and customer experience while ensuring that patient privacy is secure.

The present disclosure describes a system which may be a cloud-based application, tool, software, or device that may input patient-specific analysis data, generate or simulate models, perform analysis based on a user's input, and display or store results. A cloud-based application may enable the user to log in from anywhere.

Figure 1B:
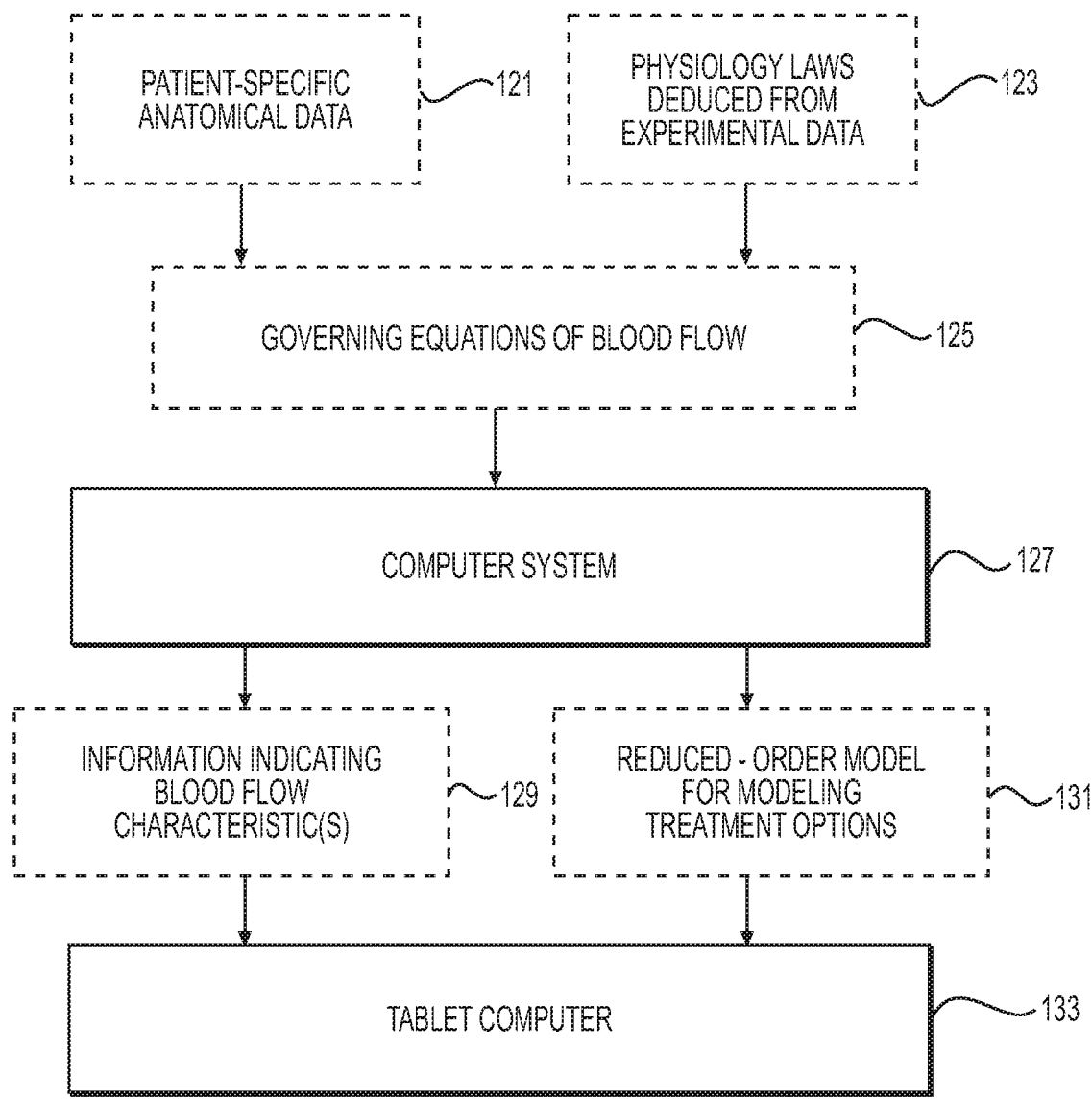
FIG. 1B is a flowchart of an exemplary method for providing diagnostic computations of the interactive diagnostic system of FIG. 1A, according to an exemplary embodiment of the present disclosure.
Figure 1C:
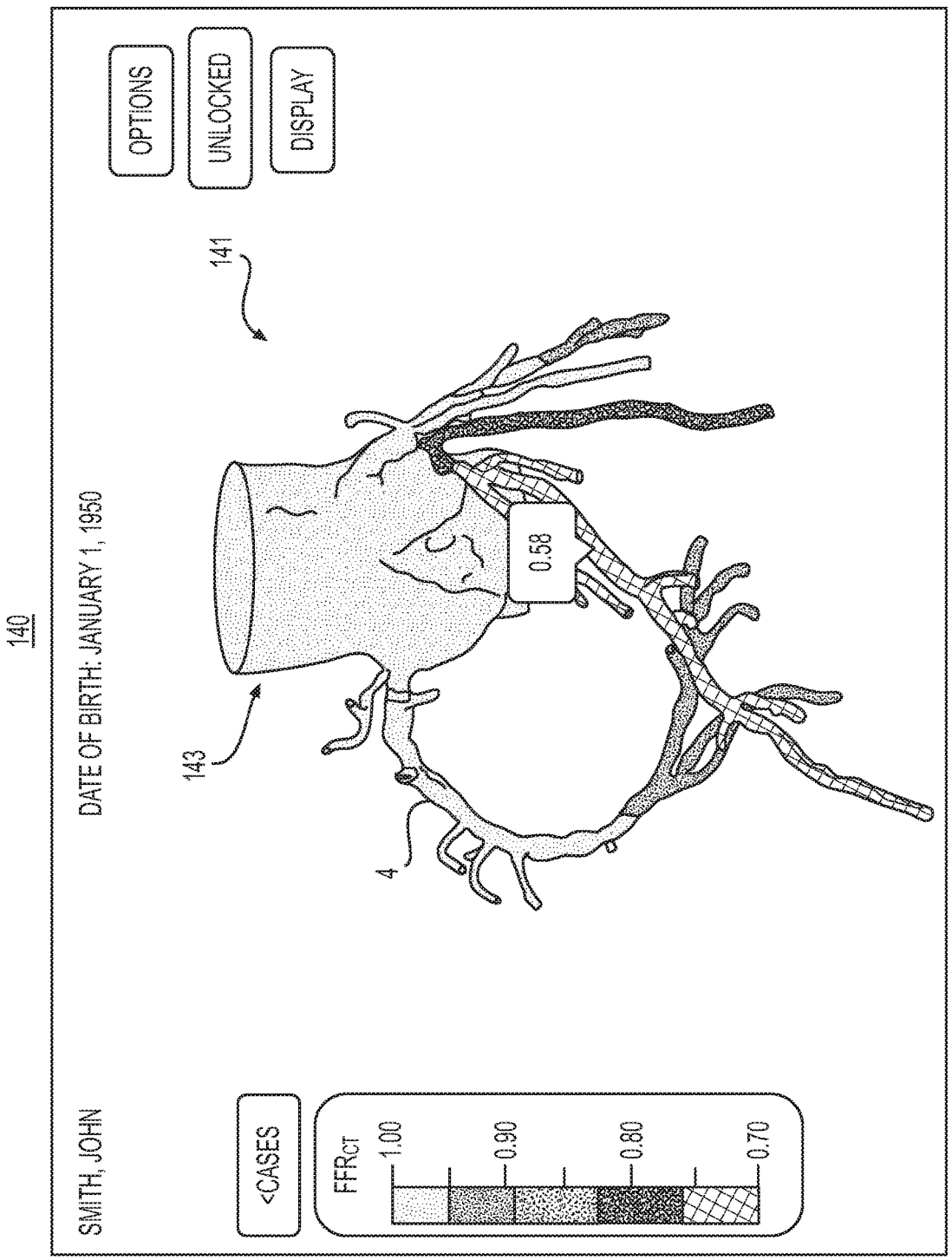
FIG. 1C is an example of a display that may be provided to a user via interactive diagnostic system 100, according to an exemplary embodiment of the present disclosure.
Figure 3:
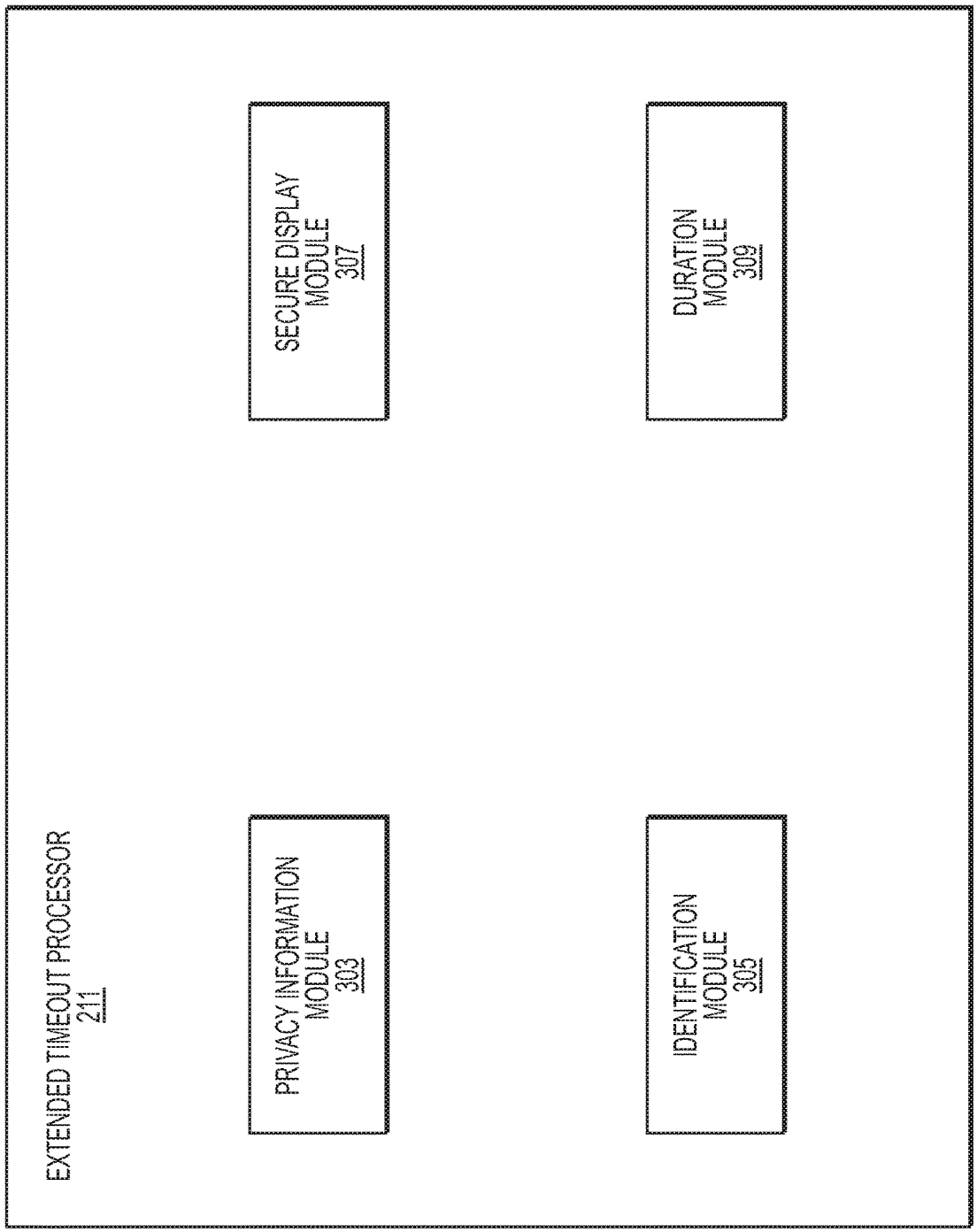
FIG. 3 is a block diagram of extended timeout processor, which may be part of a display platform, according to an exemplary embodiment of the present disclosure.
Figure 4:
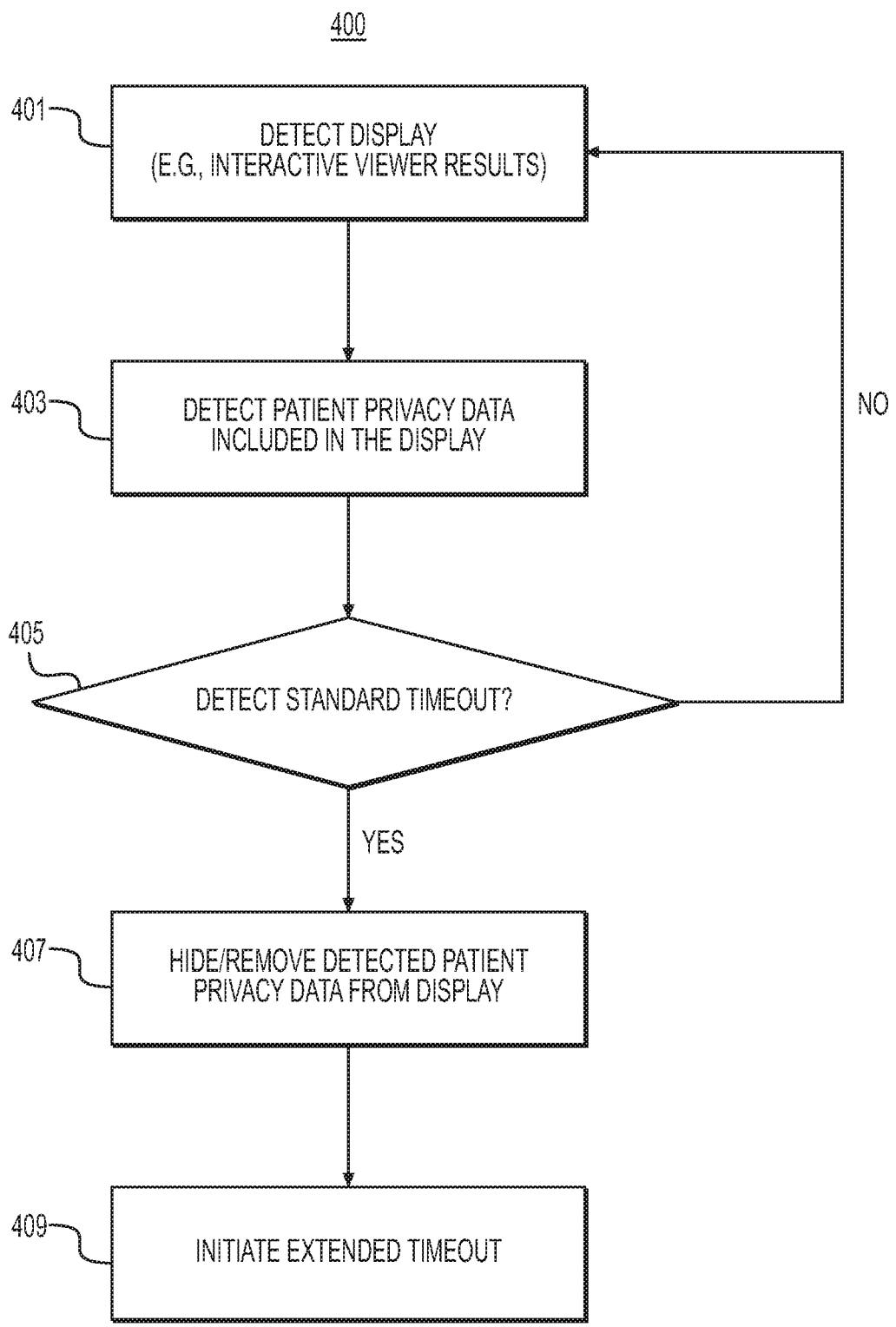
FIG. 4 is a flowchart of an exemplary method for initiating a display that preserves patient privacy (e.g., an extended timeout display), according to an exemplary embodiment of the present disclosure.
Figure 5:
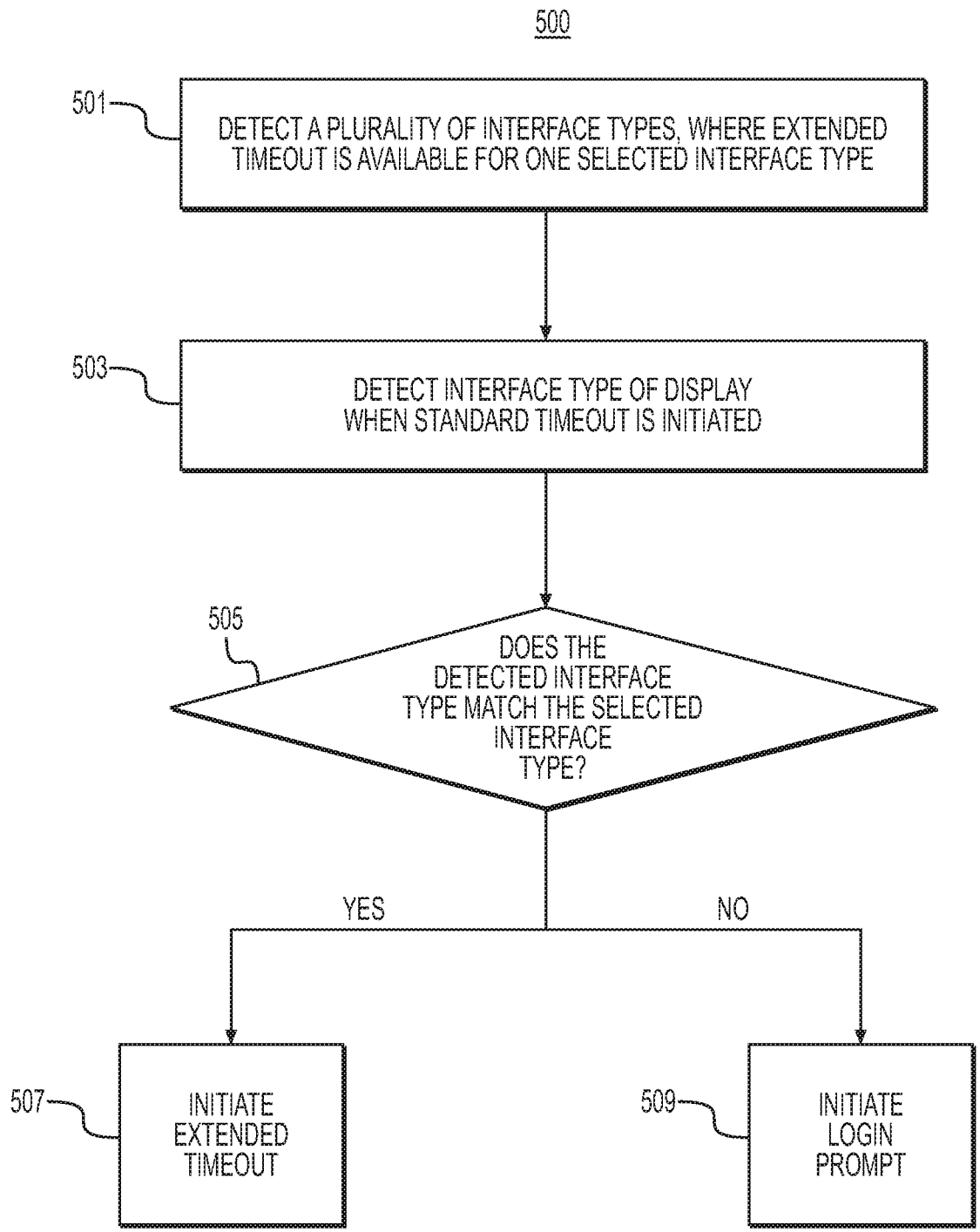
FIG. 5 is a flowchart of an exemplary method for initiating a display that preserves patient privacy, based on user interface type, according to an exemplary embodiment of the present disclosure.
Figure 6:
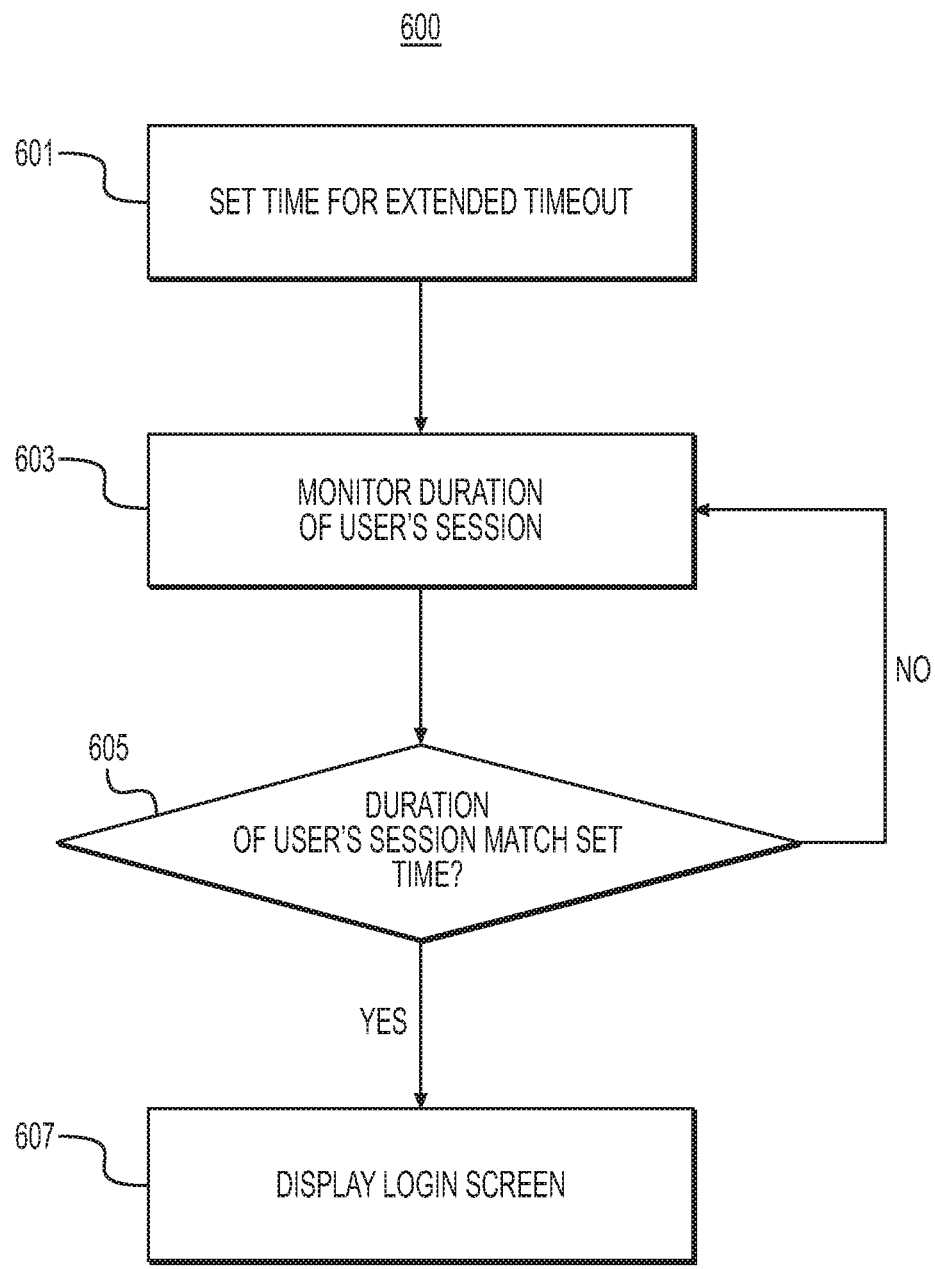
FIG. 6 is a flowchart of an exemplary method for ending a display that preserves patient privacy (e.g., an extended timeout display), according to an exemplary embodiment of the present disclosure.

FIGS. 1A-1C provide an exemplary interactive diagnostic system. Specifically, FIG. 1A presents an overview of an interactive diagnostic system that may include an extended timeout capability, while FIGS. 1B and 1C describe a particular embodiment of an interactive diagnostic system comprising a patient-specific blood flow diagnostic system. FIGS. 2 and 3 provide block diagrams that may provide extended timeout functionality for the interactive diagnostic system of FIG. 1A. FIGS. 4-6 include exemplary methods for implementing the extended timeout capability, and FIGS. 7-9B depict exemplary user interfaces that may be part of the extended timeout.

FIG. 1A depicts an exemplary interactive diagnostic system 100 offering a display. For the display, the interactive diagnostic system 100 may provide an extended timeout display that preserves patient privacy. FIG. 1B depicts a diagnostic computation system 120, which may provide one or more graphics or underlying data analyses for interactive diagnostic system 100. Diagnostic computation system 120 may be part of interactive diagnostic system 100, e.g., in producing displays for display platform 101 of interactive diagnostic system 100. Alternately, diagnostic computation system 120 may interact with interactive diagnostic system 100, providing computations or visuals that may be directly displayed via diagnostic computation system, or that may serve as the basis for displays of the interactive diagnostic system 100. FIG. 1C is an example of a display that may be provided to a user via interactive diagnostic system 100. The visualization of FIG. 1C may be generated by entirely, or in part, by diagnostic computation system 120. Each of FIGS. 1A-1C are described in further detail below.

FIG. 1A depicts a block diagram of an exemplary interactive diagnostic system 100 offering an extended timeout display that preserves patient privacy, according to an exemplary embodiment. In one embodiment, interactive diagnostic system 100 may be comprised of various components including a display platform 101, a patient privacy platform 103, a patient privacy database 107, a report database 109, a portal 111, and a network 313. Patient privacy information may include any information for securing patient privacy, e.g., patient health information (PHI).

In one embodiment, display platform 101 may perform various functions for an interactive diagnostic system. In one embodiment, display platform 101 may provide a user interface including an anatomical model, including a three-dimensional geometric model of the user's anatomy, one or more diagnostic values with color(s), shade(s), pattern(s), or other visual indicator(s) corresponding to the diagnostic values, or a combination thereof. The user interfaces may include one or more interactive displays, including colored visual indicators, graphics, charts, tables, comparisons to previous patient reports or population data, treatment recommendations, etc. Display platform 101 may further provide one or more interactive features. For example, display platform 101 may present a user interface including multiple tabs for a user to select, either to access a certain display, review a display, interact with (e.g., modify) a display, or a combination thereof. Display platform 101 is described in more detail at FIG. 2. Additional details relating to various diagnostic displays are included, for example, in U.S. Pat. No. 8,548,778 entitled "Method and System for Providing Information from a Patient-Specific Model of Blood Flow," which is incorporated by reference in its entirety.

In one embodiment, patient privacy platform 103 may detect various pieces of information that may identify a patient. Patient privacy platform 103 may further identify information that can serve as information that may provide or reveal the identity of a patient. Patient privacy information may vary by location. For instance, various countries or geographic regions may possess different requirements for protecting patient privacy. As one example, United States law seeks to protect patient privacy by defining a category of information that can link an individual's health information to the individual. This category of information is called, "protected health information (PHI)", and U.S. medical professionals and service providers (e.g., doctors, hospitals, insurance companies, covered entities, business associates, etc.) are governed by regulations that dictate usage and transfer of PHI-associated data. Other countries and regions may include analogous regulations, laws, and/or standards. Canada protects patient information at the federal and at the provincial level and Europe protects personal data (including medical information) under the General Data Protection Regulation (GDPR). Patient privacy platform 103 may detect patient identification or patient privacy information pertaining to privacy standards applying to the healthcare facility associated with display platform 101.

In one embodiment, patient privacy database 107 may store patient privacy information for the interactive diagnostic system 100. Report database 109 may store data from past interactive display sessions. Such data may include data used for the interactive sessions, analyses (e.g., reports) produced from the interactive sessions, or a combination thereof. Reports may include interactive models (in the form of files), or printable/downloadable PDF reports.

In one embodiment, portal 111 may provide access to the interfaces of display platform 101. In one embodiment, portal 311 may generate or receive notifications when a set of displays are available. Portal 311 may display a visual indicator on a user interface, showing that one or more displays (e.g., a patient analysis) are available. Portal 311 may also prompt a notification (e.g., a message received at a patient or medical professional's user device) when a report is available for access. Alternately or in addition, portal 311 may display visual indicators corresponding to the progress of an analysis or tracking the analyzed data. For example, portal 311 may display a user interface indicating, "report to be available in 3 days" or "please check back at 3 pm on Friday."

Network 113 may include the Internet, a content distribution network, or any other wired, wireless, and/or telephonic or local network. Display platform 101, patient privacy platform 103, patient privacy database 107, Report database 109, portal 111, and various user and/or administrator devices may communicate with each other via network 113. In one embodiment, users may access the display platform and/or portal 111 via network 113 and one or more devices.

Devices may include any type of electronic device configured to collect, send, and/or receive data, such as websites and multimedia content, over network 113. Devices may include medical devices, e.g., medical imaging devices, medical monitors, etc. Devices may also include one or more mobile devices, smartphones, personal digital assistants ("PDA"), tablet computers or any other kind of touchscreen-enabled device, a personal computer, a laptop, and/or server disposed in communication with network 113. Each of the devices may have a web browser and/or mobile browser installed for receiving and displaying electronic content received from one or more of web servers affiliated with data privacy system 100. The devices may include client devices that may have an operating system configured to execute a web or mobile browser, and any type of application, e.g., a mobile application. In one embodiment, various devices may be configured with network adapters to communicate data or analyzed reports over network 113. Alternatively, or additionally, various may be configured to transmit data or receive analyzed data over a local connection.

FIG. 1B shows one particular embodiment of a type of display that may comprise or interact with interactive diagnostic system 100. Specifically, FIG. 1B shows a diagnostic computation system 120 for providing various information relating to coronary blood flow in a specific patient, according to an exemplary embodiment of the present disclosure. Additional details relating to various embodiments of methods and systems for determining blood flow information in a specific patient are disclosed, for example, in U.S. Pat. No. 8,315,812 entitled "Method and System for Patient-Specific Modeling of Blood Flow," which is incorporated by reference in its entirety.

In an exemplary embodiment, a diagnostic computation system 120 may determine various information relating to blood flow in a specific patient using information retrieved from the patient. The determined information may relate to blood flow in the patient's coronary vasculature. Coronary vasculature may include a complex network of vessels ranging from large arteries to arterioles, capillaries, venules, veins, etc. The coronary vasculature circulates blood to and within the heart and includes an aorta (FIG. 1C) that supplies blood to a plurality of main coronary arteries 4 (FIG. 1C) (e.g., the left anterior descending (LAD) artery, the left circumflex (LCX) artery, the right coronary (RCA) artery, etc.), which may further divide into branches of arteries or other types of vessels downstream from the aorta 2 and the main coronary arteries 4. Thus, the exemplary method and system may determine various information relating to blood flow within the aorta, the main coronary arteries, and/or other coronary arteries or vessels downstream from the main coronary arteries. Although the aorta and coronary arteries (and the branches that extend therefrom) are discussed below, the disclosed method and system may also apply to other types of vessels. Alternatively, the determined information may relate to blood flow in other areas of the patient's vasculature, such as carotid, peripheral, abdominal, renal, and cerebral vasculature.

In an exemplary embodiment, the information determined by the disclosed methods and systems may include, but is not limited to, various blood flow characteristics or parameters, such as blood flow velocity, pressure gradient, pressure (or a ratio thereof), flow rate, and fractional flow reserve (FFR) at various locations in the aorta, the main coronary arteries, and/or other coronary arteries or vessels downstream from the main coronary arteries. This information may be used to determine whether a lesion is functionally significant and/or whether to treat the lesion, and/or to predict the results of various treatment options. This information may be determined using information obtained noninvasively from the patient. As a result, the decision whether to treat a lesion may be made without the cost and risk associated with invasive procedures.

Patient-specific anatomical data 121 may be obtained, such as data regarding the geometry of the patient's heart, e.g., at least a portion of the patient's aorta, a proximal portion of the main coronary arteries (and the branches extending therefrom) connected to the aorta, and the myocardium. The patient-specific anatomical data 121 may be obtained noninvasively, e.g., using a noninvasive imaging method. For example, CCTA is an imaging method in which a user may operate a computer tomography (CT) scanner to view and create images of structures, e.g., the myocardium, the aorta, the main coronary arteries, and other blood vessels connected thereto. Alternatively, other noninvasive imaging methods, such as magnetic resonance imaging (MRI) or ultrasound (US), or invasive imaging methods, such as digital subtraction angiography (DSA), may be used to produce images of the structures of the patient's anatomy. The resulting imaging data (e.g., provided by CCTA, MRI, etc.) may be provided by a third-party vendor, such as a radiology lab or a cardiologist, by the patient's physician, etc. Other patient-specific anatomical data 121 may also be determined from the patient noninvasively, e.g., blood pressure in the patient's brachial artery (e.g., using a pressure cuff), such as the maximum (systolic) and minimum (diastolic) pressures.

In one embodiment, diagnostic computation system 120 may provide various displays of a three-dimensional model 12 (FIG. 1C) of the patient's anatomy. The model of the patient's anatomy may be created using the patient-specific anatomical data 121. In an embodiment, the portion of the patient's anatomy that is represented by the model 12 may include at least a portion of the aorta 2 and a proximal portion of the main coronary arteries 4 (and the branches extending or emanating therefrom) connected to the aorta 2. The three-dimensional model 12 may also include other portions of the patient's anatomy, such as the left and/or right ventricles, calcium, and/or plaque within the coronary arteries 4 and/or the branches, other tissue connected to and/or surrounding the coronary arteries 4 and/or the branches, etc.

Various physiological laws or relationships 123 relating to coronary blood flow may be deduced, e.g., from experimental data. Using the model 12 and the deduced physiological laws 123, a plurality of equations 125 relating to patient-specific blood flow may be determined. For example, the equations 125 may be determined and solved using any numerical method, e.g., finite difference, finite volume, spectral, lattice Boltzmann, particle-based, level set, finite element methods, etc. The equations 125 may be solvable to determine information (e.g., pressure, pressure gradients, FFR, etc.) relating to the coronary blood flow in the patient's anatomy at various points in the anatomy represented by the model 12.

In an embodiment, the model 12 may be prepared for analysis and boundary conditions may be determined. For example, the model 12 may be trimmed and discretized into a volumetric mesh, e.g., a finite element or finite volume mesh. The volumetric mesh may be used to generate the equations 30. Boundary conditions may be determined using the physiological laws 123 and incorporated into the equations 30. The boundary conditions may provide information about the model 12 at its boundaries, e.g., the inflow boundaries, the outflow boundaries, the vessel wall boundaries, etc. The inflow boundaries may include the boundaries through which flow is directed into the anatomy of the three-dimensional model, such as at an end of the aorta near the aortic root. Each inflow boundary may be assigned, e.g., with a prescribed value or field for velocity, flow rate, pressure, or other characteristic, by coupling a heart model and/or a lumped parameter model to the boundary, etc. The outflow boundaries may include the boundaries through which flow is directed outward from the anatomy of the three-dimensional model, such as at an end of the aorta near the aortic arch, and the downstream ends of the main coronary arteries and the branches that extend therefrom. Each outflow boundary can be assigned, e.g., by coupling a lumped parameter or distributed (e.g., a one-dimensional wave propagation) model. The prescribed values for the inflow and/or outflow boundary conditions may be determined by noninvasively measuring physiologic characteristics of the patient, such as, but not limited to, cardiac output (the volume of blood flow from the heart), blood pressure, myocardial mass, etc. The vessel wall boundaries may include the physical boundaries of the aorta, the main coronary arteries, and/or other coronary arteries or vessels of the model 12.

The equations 125 may be solved using a computer system 127. Based on the solved equations 125, the computer system 127 may output information 129 indicating one or more blood flow characteristics, such as FFR, blood pressure (or pressure gradient), blood flow, or blood velocity, determined based on the solution of the equations 125. The computer system 127 may output images generated based on the model 12 and the information 129 or other results of the computational analysis, as described below. The information 129 may be determined under simulated conditions of increased coronary blood flow or hyperemia conditions, e.g., conventionally induced by intravenous administration of adenosine. For example, the boundary conditions described above may specifically model conditions of increased coronary blood flow, hyperemia conditions, and/or the effect of adenosine.

The computer system 127 may include interactive diagnostic system 100, directly provide interfaces for the interactive diagnostic system 100, or provide information that interactive diagnostic system 100 uses to provide displays. For example, after the computer system 127 solves the equations 125 as described above, the computer system 127 may create and transmit to a network (e.g., network 113 of system 100) a reduced-order (e.g., zero-dimensional or one-dimensional) model 131 for modeling various treatment options, in addition to (or instead of) the information 129 indicating the blood flow characteristics in the patient's current condition. For example, the reduced-order model 131 may be a lumped parameter model or other simplified model of the patient's anatomy that may be used to determine information about the coronary blood flow in the patient without having to solve the more complex system of equations 125 described above. The reduced-order model 131 may be created using information extracted from computed models (e.g., blood pressure, flow, or velocity information determined by solving the equations 125 described above).

In one embodiment, tablet computer 133 may be connected to a network, e.g., network 113 of interactive diagnostic system 100. A user may access portal 111 via tablet computer 133, to interact with interfaces of display platform 101.

FIG. 1C shows an exemplary interactive display 140, according to an exemplary embodiment of the present disclosure. The interactive display 140 may be rendered by display platform 101 (of interactive diagnostic system 100) on tablet 133 (of diagnostic computation system 120). In one embodiment, interactive display 140 may include computed FFR model 141 that may be output from the computer system 127. Display platform 101 may generate interactive display 140 for a user to interact with the computed diagnostic model 141. In the present case, model 141 includes a fractional flow reserve (FFR) model 141, in which FFR may be calculated as the ratio of the blood pressure at a particular location in the model 143 (e.g., in a coronary artery) divided by the blood pressure in the aorta, e.g., at the inflow boundary of the model 143. A corresponding color, shade, pattern, or other visual indicator may be assigned to the respective FFR values throughout the computed FFR model 141 such that the computed FFR model 141 may visually indicate the variations in FFR throughout the model 141 without having to visually indicate the individual numerical values for each point in the model 141.

Exemplary user interactions may include user prompts to recalculate information indicating the blood flow characteristic(s), e.g., by re-solving the equations 125 using inputs provided by the user (e.g., in selecting one or more treatment options, changing vessel geometry, changing the geometry of a treatment option (e.g., a stent), selecting a length of time for a treatment option (e.g., exercise), etc.) The display platform 101 and tablet computer 133 may receive user input and convey the information to computer system 127 for a calculation (or re-calculation) of blood flow characteristic(s). Once the calculation is complete, computer system 127 may then transmit to the network 113 the recalculated blood flow information (based on the equations 125), and display platform 101 may produce interactive displays for a user to review the recalculated blood flow information. For example, display platform 101 may generate a one or more displays of including numerical value(s) of recalculated blood flow information, a comparison of blood flow information prior to and after the recalculation, an updated version of model 143 (including geometric changes to the anatomical model due to the user's input), etc. In one embodiment, the interactive display(s) of display platform 101 be viewed or accessed via portal 11 using tablet computer 133.

FIGS. 2 and 3 depict exemplary block diagrams that may provide extended timeout functionality for the interactive diagnostic system of FIG. 1A. In particular, FIG. 2 includes an exemplary block diagram of display platform 101, which may include a standard (e.g., security) timeout processor and an extended timeout processor. FIG. 3 includes an exemplary block diagram detailing components and functions of the extended timeout processor of the display platform 101.

FIG. 2 is a block diagram 200 of display platform 101 for preparing interactive displays for medical diagnostics, according to an exemplary embodiment of the present disclosure. As shown in FIG. 2, display platform 101 may include interface module 203, monitoring module 205, and a settings module 207. In one embodiment, settings module 207 may further include standard timeout processor 209, extended timeout processor 211, and task lock processor 213. Exemplary display platform 101 may include a control logic that directs the functions and interactions among the various modules and processors that may be operating as part of display platform 101.

Figure 7:
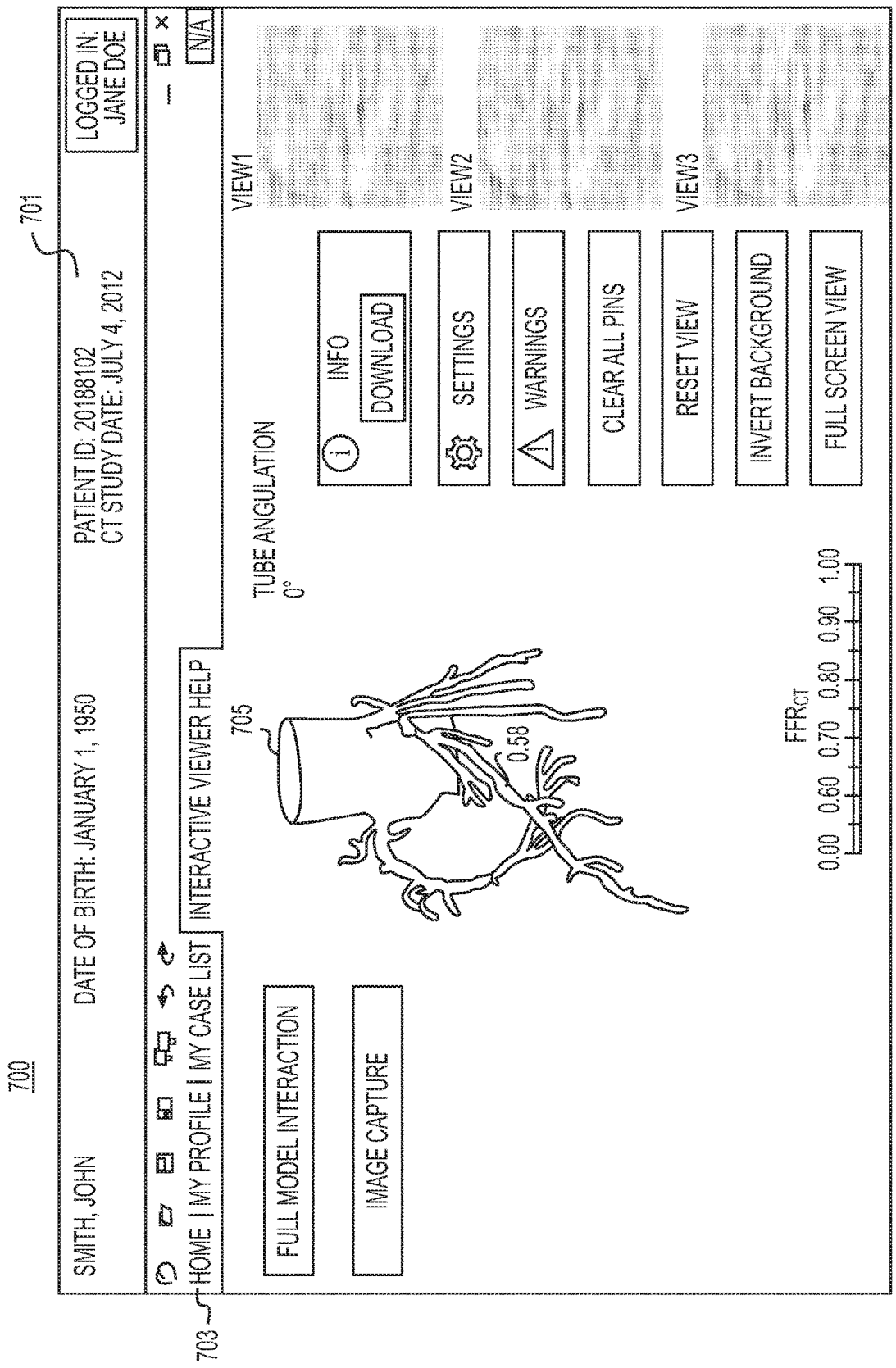
FIG. 7 is a diagram of a user interface during an active session, according to an exemplary embodiment of the present disclosure.

In one embodiment, interface module 203 may prepare a series of interfaces. For example, interface module 203 may provide a series of interfaces that a user may progress through a given session or a series of sessions. A session may include, for example, a cath lab procedure or a follow-up clinical session. In one embodiment, various interfaces may include "Home," "My Profile," "My Case List," "Interactive Viewer," and "Help." The interfaces may be provided as a series of tabs, e.g., as shown in FIG. 7. Various selections may be available in each of the interfaces. For example, "Home" may provide a range of selections for a procedure being performed, "My Profile" may provide security or interface viewing settings associated with a particular user, and/or "My Case List" may offer a listing of patients associated with the user (e.g., patients whose information is accessible to the user) or a listing of available diagnostic studies (e.g., where test results as complete and available).

In one embodiment, an "Interactive Viewer" interface may include an interface where users may modify diagnostic tools, for example, to monitor the progress of a procedure in real-time, simulate various disease treatment options (e.g., exercise or diet regimens, stent insertions, bypass grafts, etc.), evaluate risks or benefits of various treatment options, and/or compare prospective results of treatments to enhance treatment planning for the patient. Some selections may be available only in some interfaces (e.g., specific to those interfaces), while other selections may be provided across more than one interface. In one embodiment, interface module 203 may further dictate interface type. Several interfaces may be provided under one interface type. For example, "Home," "My Profile," "My Case List," "Interactive Viewer," and "Help" may each be considered an "interface type." For example, a screen with a selection of options for a user to request repair, guidance, or teaching tools with respect to tools of the interactive display platform 101 may be considered as being of the "Help" interface type.

In one embodiment, monitoring module 205 may receive user input or user interaction relative to an interface. Monitoring module 205 may detect which interface a user is on, the length of his/her session, the identity of the user, which capabilities or functions a user is presently using, etc.

In one embodiment, settings module 207 may dictate various settings available via display platform 101. In one embodiment, various settings of setting module 207 may be pre-determined. Alternately or in addition, pre-determined default settings may be adjusted by users, either during initiation or installation of the interactive diagnostic system 100 or by individual users. Among the various settings are settings for standard timeout, extended timeout, and a lock screen. In one embodiment, standard timeout processor 209 may control standard timeout for display platform 101. For example, standard timeout processor 209 may set a session duration at which timeout may be triggered. In one embodiment, a standard timeout may occur when a user has been idle for 15 minutes. For example, standard timeout processor 209 may initiate a screen lock (e.g., via task lock processor 213) if monitoring module 205 detects a user's lack of input for 15 minutes. The task lock may comprise a standard timeout. Standard timeout processor 209 may further dictate the settings of a standard timeout. For example, one embodiment may involve automatically saving a user's most recent work/session and prompting a login screen to replace the user's session.

In one embodiment, extended timeout processor 211 may govern an extended timeout session. In one embodiment, an extended timeout session may include an interactive screen that permits a user to use some interactive functions, but removes patient privacy information from the interactive display. In one embodiment, extended timeout processor 211 may be set up so that extended timeout is provided for only some interfaces, out of a plurality of interfaces that a user may use. In other words, a user may generally encounter a login screen from standard timeout for most interfaces. For a subset of interfaces, however, a user may be provided with an extended timeout session following standard timeout so that he/she may continue to work in the session. The extended timeout may present many of the same functionalities of the original session since it masks the patient privacy information.

In one embodiment, extended timeout processor 211 may dictate settings or conditions of an extended timeout. For example, extended timeout processor 211 may dictate which sessions or interactive displays provide an extended timeout, the length of an extended timeout, options for a user once an extended timeout ends, etc. FIG. 3 provides additional detail on the capabilities of extended timeout processor 211.

In one embodiment, task lock processor 213 may provide alternatives to the options of standard timeout processor 209 and extended timeout processor 211. For example, task lock processor 213 may cause some interactive capabilities to be removed from the interface, once a user is not logged in or his/her identity not verified.

FIG. 3 is a block diagram 300 of extended timeout processor 211, which may be part of display platform 101, according to an exemplary embodiment of the present disclosure. As shown in FIG. 3, extended timeout processor 211 may include interface module 203, monitoring module 205, and a settings module 207. In one embodiment, settings module 207 may further include standard timeout processor 209, extended timeout processor 211, and task lock processor 213. Exemplary extended timeout processor 211 may include a control logic that directs the functions and interactions among the various modules and processors that may be operating as part of display platform 101.

In one embodiment, privacy information module 303 may define types of data that constitute patient privacy information. Identification module 305 may detect the areas of a display that contain patient privacy information. In one embodiment, secure display module 307 may shield the areas of the display that contain patient privacy information, such that patient privacy information is not in view during an extended timeout session. Duration module 309 may set a duration for extended timeout. For example, duration module 309 may set 4 hours as the duration of an extended timeout. In one embodiment, the monitoring module 205 of the display platform 101 may monitor the duration of a user's session, including the user's session while the user is in an extended timeout. In one embodiment, duration module 309 may prompt a menu screen to replace the user's interactive session once the user's extended timeout session reaches the set duration (e.g., 4 hours). In one embodiment, the menu screen may include options, for example, "login to restore session", "print report", "download report," etc. In one scenario, duration module 309 may further prompt a series of warning screens or countdown displays as a user is nearing the end of his/her extended timeout.

FIGS. 4-6 depict exemplary methods for implementing an extended timeout session. In particular, FIG. 4 includes an exemplary method for initiating an extended timeout session. FIG. 5 includes a particular embodiment in which an extended timeout session is initiated only for a selected interface type, e.g., an "Interactive Viewer" interface. FIG. 6 includes an exemplary method for ending an extended timeout session.

FIG. 4 is a flowchart of an exemplary method for initiating a display that preserves patient privacy (e.g., an extended timeout display), according to various embodiments. In one embodiment, the display may occur during an extended timeout period. For example, upon detecting that a standard timeout has occurred, an extended timeout may begin and the display of the extended timeout may include a display with patient privacy information removed or masked. In one embodiment, step 401 may include detecting a display, e.g., an Interactive Viewer interface. Step 403 may include detecting patient privacy information included in the display. In one embodiment, patient privacy information may include PHI data. Steps 401 and 403 may be performed on an ongoing basis, until a standard timeout is detected (e.g., step 405). If standard timeout is detected, step 407 may include hiding and/or removing detected patient privacy information from the display. When the patient privacy information is hidden from view, an extended timeout session may be initiated (e.g., step 409). An extended timeout setting may include an interactive display setting in which a user may interact with some features of the display (e.g., interaction with a model, image capture, background or view manipulations (e.g., color inversions), placement or removal or pins, reset, zoom, etc.), while not having access to the patient privacy information.

FIG. 5 is a flowchart of an exemplary method for initiating a display that preserves patient privacy, based on user interface type, according to various embodiments. In one embodiment, step 501 may include detecting or designating a plurality of interface types. For example, a computerized clinical service may provide multiple types of user interfaces, e.g., a raw data upload interface/repository, a data selection, cleaning, or pre-processing interface, a progress or status check interface, a results retrieval interface, an interactive results viewing interface, a reporting interface, etc. In some cases, the option of an extended timeout may be offered in a subset of interface types. For example, extended timeout may be an option in some interface types out of the plurality of interface types, but not all of the interface types. In one scenario, step 501 may include providing extended timeout as an option while a user is at an interactive results viewing interface, but not a raw data upload or data selection interface. In one embodiment, step 503 may include detecting, for a display that a user is currently using, the interface type for the display, e.g., a "detected interface type." In some cases, initiation of standard timeout may cause step 503 to be performed.

In one embodiment, step 505 may include detecting whether the detected interface type is one of the interfaces where extended timeout is available as an option. For example, if extended timeout is offered for an interactive results viewing interface (as designated by step 501) and the user's session timed out at step 503 while the user was at the interactive results viewing interface, extended timeout may be initiated (e.g., step 507). If the user's session ended (e.g., timed out) while the user was at an interface where extended timeout is not an option, step 509 may include initiating a login prompt asking that the user sign back in, rather than initiating extending timeout. Alternately or in addition, step 509 may provide a user with options to access to a home screen or other options screen.

FIG. 6 is a flowchart of an exemplary method for ending a display that preserves patient privacy (e.g., an extended timeout display), according to various embodiments. In one embodiment, step 601 may include generating settings for an extended timeout session. For example, step 601 may include setting a duration for extended timeout, e.g., 4 hours. In one embodiment, step 603 may include determining or monitoring the amount of time a user has spent in the display may occur during an extended timeout period. Step 605 may include determining whether the amount of time a user has spent in the extended timeout period reaches the set duration for extended timeout (e.g., from step 601). If the set duration is reached, a login display may replace the extended timeout display (e.g., step 607). Step 607 may further include providing a user with download or printing options for the user's work during the extended timeout period. If the set duration is not reached, step 603 and step 605 may be repeated until the set duration is reached.

Figure 8:
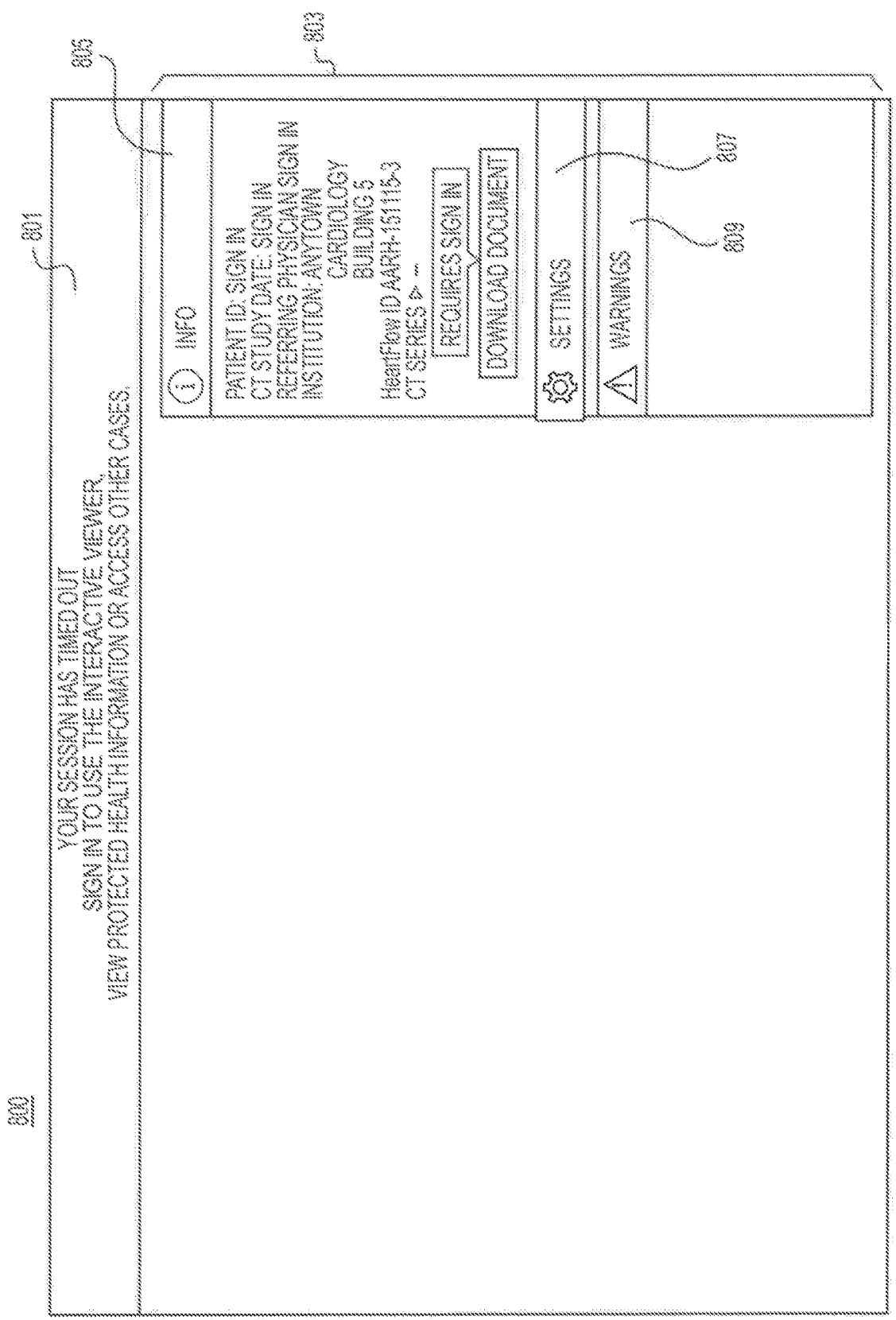
FIG. 8 is a diagram of a user interface during a standard timeout session, according to an exemplary embodiment of the present disclosure.
Figure 9A:
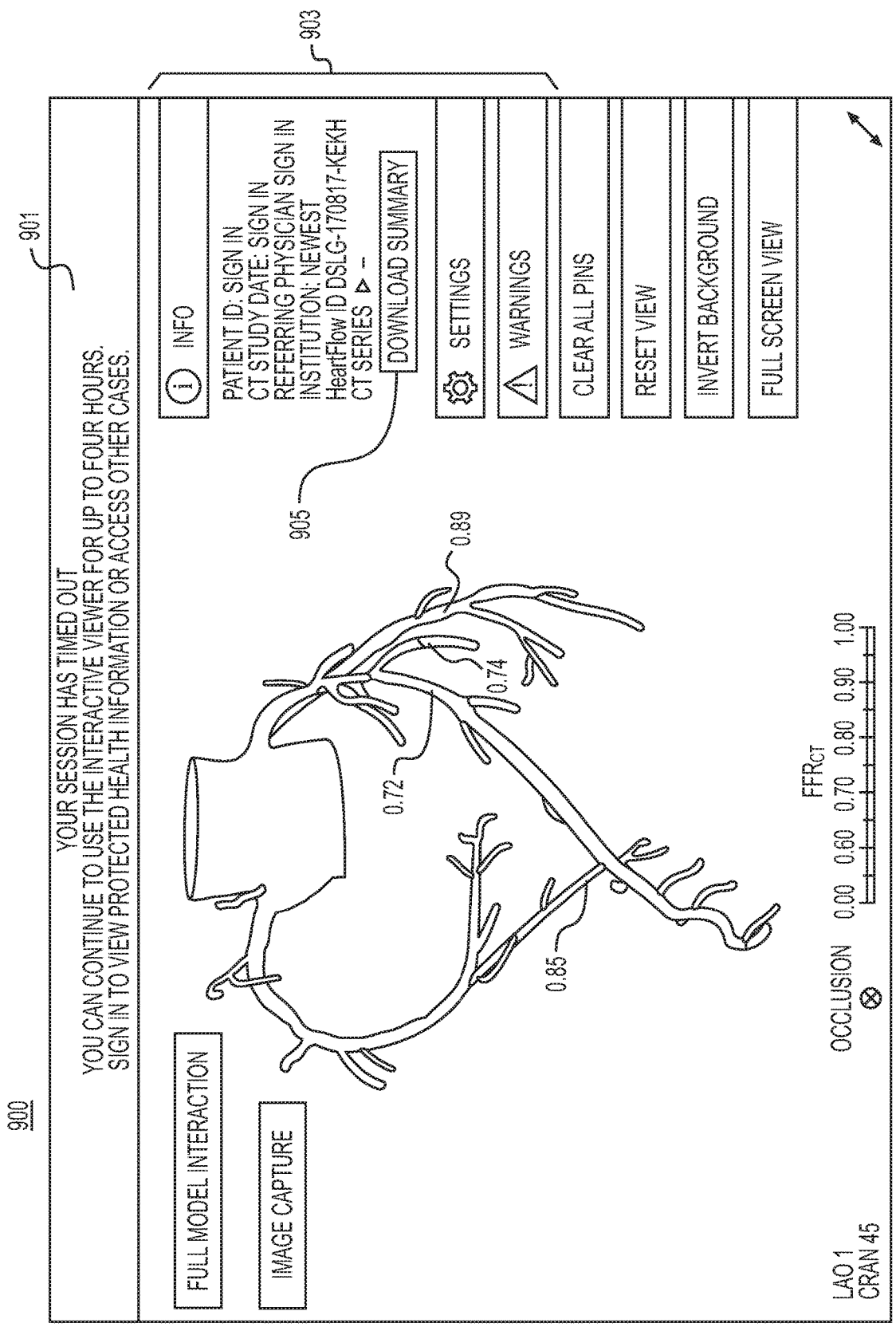
FIG. 9A is a diagram of a user interface during an extended timeout session, according to an exemplary embodiment of the present disclosure.
Figure 9B:
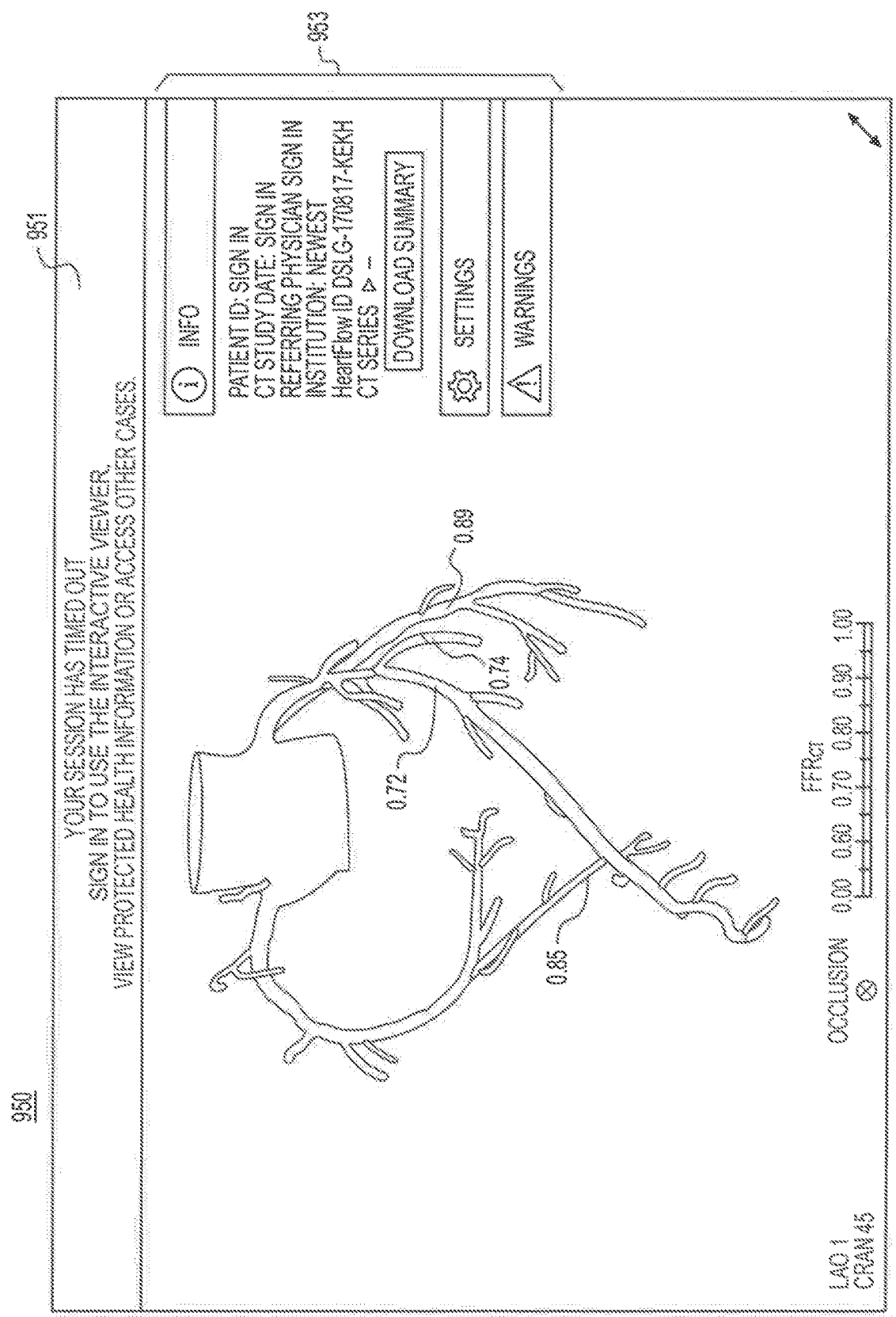
FIG. 9B is a diagram of a user interface at the end of an extended timeout session, according to an exemplary embodiment of the present disclosure.

FIG. 7 includes an exemplary user interface 700 during a standard session. FIG. 8 shows an exemplary user interface 800 for a standard timeout and FIGS. 9A and 9B show an exemplary user interface 900 for extended timeout.

In one embodiment, user interface 700 may represent an exemplary display while a user is in an active session. User interface 700 may include a header 701 containing, for example, a patient name (e.g., "John Smith"), date of birth, and/or other patient identification information (e.g., a patient identifier (assigned by a healthcare facility or the tool), a date on which data related to the patient's health was acquired (e.g., a date where computed tomography (CT) data was acquired on the patient's anatomy), etc. The header 701 may further include an indication of the user that is logged in for the active session (e.g., "Jane Doe").

Exemplary user interface 700 is an instance of a possible display while a user may be in an "Interactive Viewer" mode or interface type. As seen from menu 703, other interface types may include "Home," "My Profile," "My Case List," and "Help." In one embodiment, the "Home" interface type may offer access to various different functions or capabilities of a medical tool. "My Profile" may store a user's credentials and access information. In some cases, "My Profile" may maintain a user's access rights to information (e.g., access to some patients' profiles rather than others, ability to interact, view, or review with files, etc.). "My Case List" may provide a user with a dashboard of raw medical data available for each patient, and the possible analyses for each. For example, "My Case List" may provide a user with progress bars or other indicators of the medical data stored by the interface for each patient, and available analyses of the medical data that may be ready for the user to view or verify. "Interactive Viewer" may provide an interface where a user may interact with one or more analyses, for example, in viewing, modifying, saving, or printing/downloading the analyses or the user's modifications to the original analyses. As seen from user interface 700, the interactive viewer interface type may be denoted by the selection of the "Interactive Viewer" tab of menu 703. In some embodiments, extended timeout may be provided for a user while the user is in some interfaces and not others. For example, one embodiment may provide extended timeout for displays in the interactive viewer interface type, but not displays for "Home," "My Profile", "My Case List", or "Help."

In one embodiment, user interface 700 may include a vehicle for patient health analyses, e.g., patient anatomical model 705. User interface 700 may then provide various features for a user to employ in interacting with the vehicle/model 705. For example, features may include ways a user may work with the model, e.g., "full model interaction", which may offer ways to change the geometry of the model 705 and recalculate patient-specific diagnostic values (e.g., fractional flow reserve (FFR)), given the user's modifications to the model geometry. "Full model interaction" may also offer a menu of dropdown predictive simulations (not shown), which may provide a user with guidance for treatment. For example, predictive simulations may show changes to the model 705 (and corresponding changes to diagnostic values) if a patient undergoes noninvasive treatment (e.g., an exercise regimen), invasive treatment (e.g., stent implantation), different physiological states (e.g., medicated or exercise mode), etc. Parameters of the predictive simulations may be selected by a user. For example, the user may select a type or length/duration of an exercise regimen and prompt user interface 700 to display an update to model 705 and its corresponding diagnostic patient-specific values that may help predict the patient's response to the exercise. Similarly in the example of invasive treatment, a user may input a type of stent, a stent geometry, and/or a location of a stent and prompt user interface 700 to update model 705 and corresponding diagnostic values to help predict the outcome (e.g., success or failure) of an invasive treatment in improving a patient's condition.

User interface 700 may also provide features to a facilitate a user in working with the display of user interface 700, e.g., "Invert Background", "Full Screen View", "Reset" or "Zoom", "Clear All", or "Image Capture." Some of these features may provide capabilities particular to the display at hand, for example, "Clear All" may be "Clear All Pins," where a user interface 700 permits a user to click, touch, or otherwise select and tag portions of a display with "pins."

In one embodiment, user interface 800 may represent an exemplary display for a standard timeout. User interface 800 may include a banner 801 indicating for the user that his/her session has timed out. Options panel 803 may include various tabs, e.g., information 805, settings 807, and warnings 809. As seen by a comparison of the placement of banner 801, banner 801 may cover header 701, such that information identifying the patient may be absent from the display during timeout. In one embodiment, the information tab 805 may provide a login screen for a user to submit login credentials if they would like to continue the session with a given patient, access functionalities of the tool, or access and start an analysis for a patient other than the given patient.

Exemplary information tab 805 of options panel 803 includes prompts for a user to enter login credentials comprising, a patient identifier, a date that raw data (e.g., computed tomography imaging data) of a patient's anatomy or health condition was acquired, identification of a referring physician, the user's institution, and/or identifier for use of the tool, etc. Additional login credentials may include a user name (e.g., the user's name, alias, or other identifier for the user or his/her institution or account), a password, an authentication tool (e.g., a captcha), etc. The settings tab 807 may include an option for a user to access settings of the tool, e.g., display brightness, autosave options, download options, timings to for warnings (e.g., a 10 minute, 5 minute, and/or 1 minute warning that a session is about to expire from inactivity), default report file types (e.g., Portable Document Format (PDF), text file, spreadsheet file, image file, etc.). In one embodiment, the options of the settings tab 807 may only be accessible once a user has submitted login credentials and his/her credentials have been approved. In other words, setting tab 807 options may be available to a user only while the user is having an active (e.g., logged in session not during any timeout). Warnings tab 809 may display warnings for the user. Exemplary warnings may include, for example, notifications to a user that his/her session is about to timeout, the patient's file is being accessed by a different account, the user's login credentials are noted as being used for login at a session other than the user's current session (e.g., concurrent login), changes were made to the patient's file since the last time the user logged in to access the patient's account, etc. In one embodiment, warnings of the warnings tab 809 may be displayed for a short period of time (e.g., 5 minutes) after a user's session times out, as long as other login credentials are not received. In this kind of setup, a user of a recently-timed out session may be presumed to be near the screen and possibly interested in resuming the session. At the same time, the warnings for a previous session may not continue for so long as to interfere with another user's ability to use the tool.

In one embodiment, user interface 900 of FIG. 9A may represent an exemplary display for an extended timeout and user interface 950 of FIG. 9B may represent an exemplary display at the end of an extended timeout. As seen by a comparison of the placement of banner 901 to the placement of header 701 of user interface 700, banner 901 may cover header 701, such that information identifying the patient may be absent from the display during timeout. User interface 900 may provide many of the same features and capabilities (e.g., model interactions and viewing options) that were available during an active session. Login prompt 903 may be provided if a user attempts to access information related to a different patient, or navigate away from the "interactive viewer" interface. In one embodiment, login prompt 903 may offer a download option 905 for a user to download his/her analysis conducted during the extended timeout. In one embodiment, a user's interactions during an extended timeout period may be automatically stored, and a user logging in may have the option of either accessing the latest version of his/her work prior to standard timeout, or an auto-saved version from extended timeout.

Once the end of an extended timeout period is reached (e.g., at the end of four hours/the set duration of an extended timeout or a given period of inactivity (e.g., 20 minutes of inactivity following a standard timeout)), user interface 950 may be displayed to a user. In one embodiment, user interface 950 may still permit a passive view of an analysis, but functionalities or capabilities may be removed. Similar to banner 801 and banner 901, banner 951 masks patient privacy information and informs the user that the user is in a timeout session. If a user tries to interact with the interface (e.g., by clicking, touch, or motion), login prompt 953 may request a user's login credentials to continue his/her extended timeout session, or prompt downloading of the latest analysis (which will not be updated since features are locked or unavailable during user interface 950.

Alternately or in addition, the end of an extended timeout period may also prompt the display of user interface 800, where a display of the analysis is unavailable and user may have no option other than to log in to continue use of the tool. In one embodiment, user interface 800 may be displayed in place of user interface 950. Alternately, user interface 800 may be displayed if no user interaction is detected within a pre-set time threshold (e.g., 5 minutes) of displaying user interface 950. For example, user interface 950 may be displayed immediately as the end of an extended timeout period (e.g., 4 hours) is reached. If no user interaction is detected for 5 minutes, user interface 950 may switch to user interface 800, so that the analyses (although anonymous) is also removed from view.

To ensure compliance with patient privacy regulations and standards, interactive diagnostic tools and apps often have a standard security timeout. For many cases, the standard timeouts may activate after a user is "inactive" for 15 minutes. However, users often do not interact continuously with tools/apps during procedures, so being timed out of a work session continuously may be frustrating and inconvenient to users and patients. Users may lose their work product during the timeout and procedures may take longer when users are forced to log in again and again. At the same time, patients, healthcare professionals, and security personnel want to maintain high standards for protecting patient privacy information and prevent a scenario where an unused tool/app continues to expose patient privacy information. An extended timeout may protect patient privacy, while providing an uninterrupted work session. An extended timeout may appear as a display after a standard timeout, removing patient privacy information from a display while still permitting users to access some functionalities of diagnostic tools/apps. In some cases, the extended timeout display may be initiated even without a standard timeout, for instance, if a user would like to shield patient privacy information from another party, yet still share a portion of an analysis.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer-implemented method of performing a diagnostic procedure on a patient using a diagnostic tool, the method comprising:
    displaying, on a display of the diagnostic tool, an interactive interface of the diagnostic tool for the diagnostic procedure:
    determining whether the interactive interface has been displayed for a first predetermined period of time without interaction from a user;
    in response to determining that the interactive interface has been displayed for a first predetermined period of time without interaction from the user:
        identifying patient privacy information of the patient included in the interactive interface; and
        obscuring the identified patient privacy information from the interactive interface; and
    during a period of time in which the identified patient privacy information is obscured:
        receiving an interaction from the user that causes the diagnostic tool to perform a diagnostic action; and
        updating the interactive interface based on the performed diagnostic action without revealing the obscured patient privacy information.

2. The computer-implemented method of claim 1, further comprising:
    in response to determining that the interactive interface has been displayed for a second predetermined period of time without interaction from the user, the second period of time being longer than the first predetermined period of time, obscuring an entirety of the interactive interface and preventing the diagnostic tool from receiving an interaction from the user that causes the diagnostic tool to perform a diagnostic action.

3. The computer-implemented method of claim 2, further comprising:
    displaying a login screen on the display of the diagnostic tool; and
    in response to receiving a login action of the user via the login screen, revealing the interactive interface, including the patient privacy information, and re-enabling the diagnostic tool to receive an interaction from the user that causes the diagnostic tool to perform a diagnostic action.

4. The computer-implemented method of claim 3, wherein:
    updating the interactive interface based on the performed diagnostic action without revealing the obscured patient privacy information includes updating at least a portion of the patient privacy information without revealing the obscured patient privacy information; and
    revealing the interactive interface includes revealing the updated at least portion of the patient privacy information.

5. The computer-implemented method of claim 1, wherein:
    the interactive interface of the diagnostic tool for the diagnostic procedure is one of a plurality of different interfaces that are selectively displayed by the display.

6. The computer-implemented method of claim 5, further comprising:
    in response to determining that at least one of the plurality of different interfaces other than the interactive interface of the diagnostic tool for the diagnostic procedure has been displayed for the first predetermined period of time without interaction from the user, displaying one or more of a login prompt or option, a disclaimer, or a navigation option.

7. A diagnostic tool for performing a diagnostic procedure on a patient, the diagnostic tool comprising:
    at least one processor;
    at least one display operatively connected to the at least one processor; and
    at least one memory operatively connected to the processor, and storing instructions that are executable by the processor and configured to cause the processor to perform acts, including:
        displaying, on the display, an interactive interface of the diagnostic tool for the diagnostic procedure:
        determining whether the interactive interface has been displayed for a first predetermined period of time without interaction from a user;
        in response to determining that the interactive interface has been displayed for a first predetermined period of time without interaction from the user:
            identifying patient privacy information of the patient included in the interactive interface; and
            obscuring the identified patient privacy information from the interactive interface; and
        during a period of time in which the identified patient privacy information is obscured:
            receiving an interaction from the user that causes the diagnostic tool to perform a diagnostic action; and
            updating the interactive interface based on the performed diagnostic action without revealing the obscured patient privacy information.

8. The diagnostic tool of claim 7, wherein the acts further include:
    in response to determining that the interactive interface has been displayed for a second predetermined period of time without interaction from the user, the second period of time being longer than the first predetermined period of time, obscuring an entirety of the interactive interface and preventing the diagnostic tool from receiving an interaction from the user that causes the diagnostic tool to perform a diagnostic action.

9. The diagnostic tool of claim 8, wherein the acts further include:
    displaying a login screen on the display of the diagnostic tool; and
    in response to receiving a login action of the user via the login screen, revealing the interactive interface, including the patient privacy information, and re-enabling the diagnostic tool to receive an interaction from the user that causes the diagnostic tool to perform a diagnostic action.

10. The diagnostic tool of claim 9, wherein:
updating the interactive interface based on the performed diagnostic action without revealing the obscured patient privacy information includes updating at least a portion of the patient privacy information without revealing the obscured patient privacy information; and
revealing the interactive interface includes revealing the updated at least portion of the patient privacy information.

11. The diagnostic tool of claim 7, wherein:
the interactive interface of the diagnostic tool for the diagnostic procedure is one of a plurality of different interfaces that are selectively displayed by the display.

12. The diagnostic tool of claim 11, wherein the acts further include:
in response to determining that at least one of the plurality of different interfaces other than the interactive interface of the diagnostic tool for the diagnostic procedure has been displayed for the first predetermined period of time without interaction from the user, displaying one or more of a login prompt or option, a disclaimer, or a navigation option.

13. A non-transitory computer readable medium for use on a diagnostic tool containing computer-executable programming instructions for operating an interactive interface of the diagnostic tool for performing a diagnostic procedure on a patient, the instructions executable by a processor to preform acts, including:
displaying, on a display of the diagnostic tool, the interactive interface;
determining whether the interactive interface has been displayed for a first predetermined period of time without interaction from a user;
in response to determining that the interactive interface has been displayed for a first predetermined period of time without interaction from the user:
identifying patient privacy information of the patient included in the interactive interface; and
obscuring the identified patient privacy information from the interactive interface; and
during a period of time in which the identified patient privacy information is obscured:
receiving an interaction from the user that causes the diagnostic tool to perform a diagnostic action; and
updating the interactive interface based on the performed diagnostic action without revealing the obscured patient privacy information.

14. The computer readable medium of claim 13, wherein the acts further include:
in response to determining that the interactive interface has been displayed for a second predetermined period of time without interaction from the user, the second period of time being longer than the first predetermined period of time, obscuring an entirety of the interactive interface and preventing the diagnostic tool from receiving an interaction from the user that causes the diagnostic tool to perform a diagnostic action.

15. The computer readable medium of claim 14, wherein the acts further include:
displaying a login screen on the display of the diagnostic tool; and
in response to receiving a login action of the user via the login screen, revealing the interactive interface, including the patient privacy information, and re-enabling the diagnostic tool to receive an interaction from the user that causes the diagnostic tool to perform a diagnostic action.

16. The computer readable medium of claim 15, wherein:
updating the interactive interface based on the performed diagnostic action without revealing the obscured patient privacy information includes updating at least a portion of the patient privacy information without revealing the obscured patient privacy information; and
revealing the interactive interface includes revealing the updated at least portion of the patient privacy information.

17. The computer readable medium of claim 13, wherein:
the interactive interface of the diagnostic tool for the diagnostic procedure is one of a plurality of different interfaces that are selectively displayed by the display.

18. The computer readable medium of claim 17, wherein the acts further include:
in response to determining that at least one of the plurality of different interfaces other than the interactive interface of the diagnostic tool for the diagnostic procedure has been displayed for the first predetermined period of time without interaction from the user, displaying one or more of a login prompt or option, a disclaimer, or a navigation option.

* * * * *